United States Patent [19]

Sih

[11] Patent Number: 5,077,407

[45] Date of Patent: Dec. 31, 1991

[54] SUBSTITUTED 2-[MONOANNELATED (3,4-,4,5-, AND 5,6-) PYRIDYLALKYLENESULFINYL]BENZIMIDAZOLES

[75] Inventor: John C. Sih, Kalamazoo, Mich.

[73] Assignee: The Upjohn Company, Kalamazoo, Mich.

[21] Appl. No.: 266,291

[22] Filed: Oct. 31, 1988

Related U.S. Application Data

[63] Continuation of Ser. No. 617,419, Jun. 5, 1984, abandoned, which is a continuation-in-part of Ser. No. 510,468, Jul. 1, 1983, abandoned.

[51] Int. Cl.[5] .................. C07D 491/04; C07D 495/04

[52] U.S. Cl. .................................... 546/116; 546/117

[58] Field of Search ................ 546/116, 117; 514/301, 514/302

[56] References Cited

U.S. PATENT DOCUMENTS 4,011,228 3/1977 Curron .............................. 546/176
4,045,563 8/1977 Berntsson et al. .................. 514/338
4,255,431 3/1981 Junggren et al. ............... 546/271 X
4,359,465 11/1982 Ruwart .............................. 424/263

FOREIGN PATENT DOCUMENTS 8300736 9/1983 Sweden .
2134523 2/1984 United Kingdom .

*Primary Examiner*—David B. Springer
*Attorney, Agent, or Firm*—Lawrence T. Welch

[57] ABSTRACT

The present invention provides novel substituted 2-[monoannelated(3,4- 4,5-, and 5,6-)pyridylalkylenesulfinyl]-benzimidazoles with gastric acid inhibiting effects.

8 Claims, No Drawings

SUBSTITUTED 2-[MONOANNELATED (3,4-,4,5-, AND 5,6-) PYRIDYLALKYLENESULFINYL]BENZIMIDAZOLES

CROSS-REFERENCE TO RELATED APPLICATION

This application is a continuation of Ser. No. 607,419 filed Jun. 5, 1984, which is a continuation-in-part of application Ser. No. 510,468, filed July 1, 1983, both abandoned.

DESCRIPTION

BACKGROUND OF THE INVENTION

The present invention involves novel compositions of matter. More particularly, the present invention involves novel substituted 2-[monoannelated(3,4-, 4,5-, and 5,6-)pyridylalkylenesulfinyl]-benzimidazoles which are useful as gastric antisecretory and cytoprotective agents.

Gastrointestinal inflammatory diseases are characterized by inflammation, specifically by the presence of edema, characteristic inflammatory cells (i.e., leucocytes, histiocytes, and macrophages), and, in some cases, necrosis and ulceration of the surface epithelium. These inflammatory diseases are known to be caused by a wide variety of agents present in the gastrointestinal tract which are known to attack the surfaces thereof, producing the inflammatory disease response. Such agents include micro-organisms (viruses and fungi), bacterial toxins, certain pharmaceutical agents (antibiotics and anti-inflammatory steroids), and chemical agents (bile salts, toxic household chemicals). Gastric acid itself is also capable of attacking the stomach lining and producing an inflammatory state.

One means of preventing or treating certain gastrointestinal diseases, specifically gastric diseases, is by the inhibition of gastric acid secretion. In situations where the integrity of the gastric mucosal barrier is compromised, gastric acid secretion can result in erosion of the epithelial cells with consequent inflammation and ulceration. Inhibition of such untoward gastric acid-induced effects can be achieved by the administration of a pharmacological agent effective to inhibit gastric secretion.

One class of such agents effective to inhibit gastric acid secretion are the gastric antisecretory prostaglandins. These substances are known to be effective in the treatment and care of gastric and duodenal ulcers as a result of the inhibition of gastric secretion. See, e.g., U.S. Pat. No. 3,903,297 (Robert, "Method of Treatment and Prophylaxis of Gastric Hypersecretion and Gastric Duodenal Ulcers Using Prostaglandin Analogs"), and Robert, "Antisecretory Property of Prostaglandins," Prostaglandin Symposium of the Worcester Foundation for Experimental Biology 16–17 October 1967, Interscience, New York, page 47 (1978). Another important class of antisecretory agents are the histamine $H_2$ receptor antagonists, including metiamide and most importantly cimetidine, N-cyano-N'-methyl-N"[2-[[(5-methyl-1H-imidazole-4-yl)methyl]thio]ethyl]guanidine. See, the Merck Index, 9th Edition, Appendix, page App-1 (1976), and Physician's Desk Reference, 36th Edition, 1812–1814 (1982).

Another means of treating such gastrointestinal diseases is through cytoprotection. Certain pharmacological agents have heretofore been known to be useful in exerting a cytoprotective effect on the gastrointestinal tract. This cytoprotective effect is manifest in the ability of such compounds to treat or prevent non-traumatically-induced, non-neoplastic inflammatory disease of the gastrointestinal tract. References describing such cytoprotective effects of prostaglandins are U.S. Pat. No. 4,083,998 (Robert, "Treatment of Inflammatory Diseases of the Mammalian Large Intestine with Cytoprotective Prostaglandins"), issued Apr. 11, 1978, U.S. Pat. No. 4,081,553 (Robert, "Cytoprotective Prostaglandins for Use in Intestinal Diseases"), issued Mar. 28, 1978, and U.S. Pat. No. 4,097,603 (Robert, "Gastric Cytoprotection with Non-Antisecretory Doses of Prostaglandins"), issued June 27, 1978. Gastric cytoprotection is a distinct pharmacological property which is unrelated to gastric antisecretory effects. See, e.g., Robert, U.S. Pat. No. 4,097,603, "Gastric Cytoprotection With Non-Antisecretory Doses of Prostaglandins," Robert, "Cytoprotection by Prostaglandins," Gastroenterology 77:761–767 (1979), Robert, "Current History of Cytoprotection," Prostaglandins 21 (supp):89 (1981), and Robert, et al., "Cytoprotection by Prostaglandins in Rats," Gastroenterology, 77:433–443 (1979). Thus, compounds which are gastric anti-secretory agents may not be cytoprotective agents and vice-versa.

Prior Art

U.S. Pat. No. 4,045,563 discloses certain substituted 2-[pyridylalkylenesulfinyl]-benzimidazoles having gastric acid secretion inhibiting effects. U.S. Patent 4,255,431 discloses certain 2-(2-benzimidazolyl)-pyridines which are useful in inhibiting gastric secretion. Finally, U.S. Pat. No. 4,359,465 discloses the cytoprotective use of certain heterocyclyalkylsulfinylbenzimidazoles.

SUMMARY OF THE INVENTION The present invention particularly provides: a compound of the formula I, wherein X is
(a) =S, or
(b) =SO;

wherein A and B are the same or different and are
(a) hydrogen,
(b) $-OR_1$,
(c) $-COR_1$,
(d) $-CO_2R_1$, or
(e) $-CO_2M$;

wherein $R_1$ is $C_1$–$C_4$ alkyl;
wherein M is a pharmacologically acceptable cation;
wherein D is a bicyclic substituent of the formula II, III, or IV;
wherein V is
(a) =O,
(b) =S, or
(c) $=CH_2$; and
wherein n is zero or one.

The carbon atom content of various hydrocarbon-containing moieties is indicated by a prefix designating the minimum and maximum number of carbon atoms in the moeity, i.e., the prefix ($C_i$–$C_j$) indicates a moiety of the integer "i" to the integer "j" carbon atoms, inclusive. Thus ($C_1$–$C_4$) alkyl refers to alkyl of one to 4 carbon atoms, inclusive, or methyl, ethyl, propyl, butyl, and isomeric forms thereof.

The compounds of the present invention may be in the form of pharmacologically acceptable salts. These salts are formed when at least one of A and B is $CO_2M$ (with M being a pharmacologically acceptable cation).

Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine,
4-ethylmorpholine,
1-isopropylpyrrolidine,
2-methylpyrrolidine,
1,4-dimethylpiperazine,
2-methylpiperidine, and the like, as well as amines containing water-solubilizing or hydrophilic groups, e.g, mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
galactamine,
N-methylglycamine,
N-methylglucosamine,
ephedrine,
phenylephrine,
epinephrine,
procaine, and the like. Further useful amine salts are the basic amino acid salts, e.g., lysine and
arginine Examples of suitable pharmacologically acceptable quaternary ammonium cations are tetramethylammonium,
tetraethylammonium,
benzyltrimethylammonium,
phenyltriethylammonium, and the like.

The compounds of the present invention will be named herein using the Chemical Abstracts numbering system (see Naming and Indexing of Chemical Substances for Chemical Abstracts during the Ninth Collective Period (1972–1976), a reprint of section IV from the Volume 76 Index Guide.)

Compounds of this invention have been tested in one or more standard laboratory tests which demonstrate gastric antisecretory activity. Thus, compounds of this invention have been shown to be effective as inhibitors of $K^+$—dependent ATP hydrolysis by isolated hog gastric membranes enriched with gastric($H^+-K^+$)ATP-ase. In this system, 2-[(6-azachroman-5-yl)methyl]sulfinyl-5-methoxybenzimidazole (Example 6) has been shown to be the most effective with an $ED_{50}$ of $1\times10^{-5}$ molar In a test for in vivo inactivation of ($H^+-K^+$)ATP-ase in the rat 2-[(6-azachroman-5-yl)methyl]sulfinyl-5-methoxybenzimidazole (Example 6), was shown to be the most effective, having an $ED_{50}$ of 1 mg/kg when administered subcutaneously. Further, these compounds have been shown to be active as inhibitors of gastric acid secretion in rats both subcutaneously and intraduodenally. In these test systems one compound was found to be the most effective, 2-[(6-azachroman-5-yl)methyl]sulfinyl-5-methoxybenzimidazole (Example 6), having an $ED_{50}$ in the rat gastric antisecretory assay, administered intraduodenally, of 0.7 mg per kg. 2-[(5,6,7,8-tetrahydroisoquinoline-1-yl)methyl]-sulfinyl-5-methoxybenzimidazole (Example 4) exhibited an $ED_{50}$ of 1.8 mg/kg when administered subcutaneously. Compounds of this invention have been shown to be active as inhibitors of acid secretion in isolated gastric glands of the rabbit. In this system, 2-[(5,6,7,8-tetrahydroisoquinoline-1-yl)methyl]sulfinyl-5-methoxybenzimidazole (Example 4) was shown to be the most effective with an $ID_{50}$ of $8\times10^{-7}$ molar.

Certain of the compounds of this invention are preferred because of their long duration of action when administered parenterally (e.g., subcutaneously). Thus, 2-[(5,6,7,8-tetrahydroisoquinolin-1-ylmethyl)sulfinyl]-benzimidazole and 2-[(5-thia-5, 6, 7, 8-tetrahydroisoquinolin-1-ylmethyl)-sulfinyl]benzimidazol when administered at 10 mg/kg subcutaneously inhibited rat gastric ($H^++K^{30}$) ATPase activity with t1/2 of 4 days and 2 days, respectively.

In general, the preferred compounds of this invention are those of the formula I wherein A and B are hydrogen, X is =SO, and D is a bicyclic substitutent of the formula II.

All of the compounds of this invention are useful as gastric antisecretory agents.

Compounds of this invention are administered for gastric antisecretory purposes orally, parenterally, (e.g., intravenously, subcutaneously, intramuscularly or intraparenterally), rectally, or vaginally in forms such as pills, capsules, solutions, suspensions, suppositories, or bougies. The compounds of this invention are formulated into these pharmaceutical compositions by means known to the pharmaceutical art.

An ordinarily skilled physician can readily determine persons suffering from gastrointestinal diseases characterized by the gastric-acid induced effects noted above. These conditions are treated using the compounds of the present invention.

Typical dose ranges for the compounds of this invention range from about 0.01 μg per kg to about 250 mg per kg, preferably from about 0.1 to 100 mg per kg. The choice of the use, route, and frequency of administration of the compounds of this invention depends on the weight, age, and gastrointestinal disease of the patient and the particular compound employed. These decisions are readily made by a physician of ordinary skill in the art.

The compounds of this invention may also exert cytoprotective effects. If employed for this purpose, they could be administered as described, for example, in U.S. Pat. No. 4,359,465, particularly cols. 7 and 8 thereof. The doses employed for this purpose would in general be less than those used for gastric antisecretory effects.

The compounds of the present invention are prepared by the methods depicted in Charts A-H. In the Charts, A, B, V, and D, and n are defined as described above and X is $—OSO_2CH_3$ or —Cl.

Chart A depicts the general schemes for preparing the compounds of this invention. In scheme 1, a 2-mercaptobenzimidazole of the formula A-1 is reacted with a chloride or methanesulfonyl compound of the formula A-2 to yield the formula A-3 product. Compounds of the formula A-1 are well known and are available commercially or may be prepared by the method of Chart H. Compounds of the formula A-3 are also known or may be prepared by the methods of Charts B through G. The formula A-3 product, which encompasses the formula I compounds wherein X is =S, may be converted to compounds wherein X is =SO by treating the formula A-3 thioether with m-chloroperbenzoic acid to yield the formula A-4 sulfoxide compound. One equivalent of sodium bicarbonate is preferably added to the reaction mixture prior to the addition of the peracid to prevent decomposition of the final product by the m-chlorobenzoic acid which is formed during the reaction.

In scheme 2 of Chart A, a benzimidazole compound of the formula A-5 (wherein M is potassium, sodium, or lithium) is reacted with the chlorinated compound of the formula A-6 to yield the formula A-4 product. The formula A-5 compounds are known and are prepared as described in U.S. Pat. Nos. 4,045,563; 4,255,431; and 4,337,257; all of which are incorporated herein by reference. The chlorinated compounds of the formula A-6 are prepared by reacting the N-oxide intermediates of Charts B-I with known chlorinating agents (e.g., $POCl_3$, $PCl_3$, and $PCl_5$).

In scheme 3 of Chart A, a chlorinated benzimidazole of the formula A-7 is reacted with the formula A-8 thiol to yield the formula A-3 product which is converted to the formula A-4 product as described above. The formula A-7 and A-8 compounds are known ar may be prepared by the methods described in U.S. Pat. Nos. 4,045,563; 4,255,431; and 4,337,257, using the intermediates prepared as described herein.

In scheme 4 of Chart A, the diamino compound of the formula A-9 is reacted with the formula A-10 acid to yield the formula A-3 product which is converted to the formula A-4 product as described above. The formula A-9 and A-10 compounds are known or may be prepared as described in U.S. Pat. Nos. 4,045,563; 4,255,431; and 4,337,257; using the intermediates prepared as described herein.

The reaction of A-1 with A-2 (Chart A, scheme 1) is carried out in a manner which is known in the art in suitable, preferably polar solvents (such as methanol, dimethylsulfoxide, acetone, dimethylformamide or acetone) with the addition or exclusion of water. It is carried out for example in the presence of a proton acceptor. Examples of suitable proton acceptors are alkali metal hydroxides, such as sodium hydroxide, alkali metal carbonates, such as potassium carbonate, and tertiary amines, such as pyridine, triethylamine or ethyl diisopropylamine. The reaction temperature can be between 0° and 150° C, temperatures between 50° and 100° C, and especially the boiling point of the solvent used, being preferred.

Similar reaction conditions to those for the reaction of A-1 with A-2 are used in the reaction of A-7 with A-8 (Chart A, scheme 3) which is carried out in a manner which is known in the art.

The reaction of A-9 with A-10 (Chart A, scheme 4) is preferably carried out in polar, optionally water-containing solvents in the presence of a strong acid, for example hydrochloric acid, in particular at the boiling point of the solvent used.

The oxidation of sulfides A-3 is carried out in a manner which is known per se and under conditions with which those skilled in the art are familiar for the oxidation of sulfides to give sulfoxides. Possible oxidizing agents are all the reagents usually employed for oxidation of sulfides, in particular peroxyacids, such as for example, peroxyacetic acid, trifluoroperoxyacetic acid, 3,5-dinitroperoxybenzoic acid, peroxymaleic acid or, preferably m-chloroperoxybenzoic acid. The reaction is expediently carried out in inert solvents, for example aromatic or chlorinated hydrocarbons, such as benzene, toluene, methylene chloride or chloroform. The reaction temperature is between −70° C. and the boiling point of the solvent used, but preferably between −30° C. and +20° C. (depending on the reactivity of the oxidizing agent and the degree of dilution). The oxidation with halogens or hypohalogenites (e.g., with aqueous sodium hypochloride solution), which is carried out expediently at temperatures between 0° and 30° C. has also proved to be very advantageous.

The reaction of A-5 with A-6 (Chart A, scheme 2) is preferably carried out in inert solvents, such as those which are also usually employed for the reaction of enulate ions with alkylating agents. Examples which may be mentioned are aromatic solvents, such as benzene or toluene. The reaction temperature is as a rule between 0° and 120° C (depending on the nature of the alkali metal atom M) preferably at the boiling point of the solvent. For example, if M represents Li (lithium) and the reaction is carried out in benzene, the boiling point of benzene (80° C.) is preferred.

Chart B depicts a method for preparing formula A-2 compounds. A methylated compound of the formula B-1(a), B-1(b), or B-1(c), (corresponding to substituents II, III, and IV within the scope of D) is treated with acetic acid and hydrogen peroxide or metachloroperbenzoic acid to yield the formula B-2 N-oxide. This compound is then treated with acetic anhydride to yield the formula B-3 acetate. This acetate is then hydrolyzed to the corresponding alcohol by conventional means (e.g., sodium methoxide in methanol). The formula B-4 alcohol is then converted to the chloride by treatment in methylene chloride with methanesulfonyl chloride and triethylamine.

Chart C depicts a method for preparing compounds of the formulas B-1(a), B-1(b), and B-1(c) wherein V is $=CH_2$ and n is one. An isoquinoline compound of the formula C-1, with or without methyl substitution, is hydrogenated under strong acidic conditions using a Parr apparatus and 85% platinum oxide catalyst. Unsubstituted isoquinoline compounds may be methylated by conventional means, e.g., by treatment with methyllithium in diethyl ether. This procedure is also described in Vierhapper, et al., J. Org. Chem. 40:2729 (1975).

Chart D, E and F depict methods for preparing the oxa-annelated pyridine intermediates. In Chart D, a compound of the formula D-1 (which is available commercially or can be prepared by known means is treated with ethyl bromoacetate or ethyl acrylate to obtain the formula D-2 compound wherein n is zero or 1, respectively. This compound is then treated successively with lithium aluminum hydride, and a strong acid (e.g., sulfuric acid) to the formula D-3 compound. This alcohol is treated with p-toluene sulfonic acid to yield the formula D-4 compound. This unsaturated compound is treated with xylene in the presence of a palladium-on-carbon catalyst to yield the formula D-5 compound which is alkylated by conventional means (e.g., methyllithium) to yield the formula D-6 compound. The conversion of D-1 to D-5 is described in Sliwa, J. Het. Chem. 12:809 (1975). This procedure is modified using ethyl bromoacetate to obtain Formula D-6 compounds wherein n is 0.

In Chart E, a compound of the formula E-1, a well-known and readily available compound, is treated succesively with mercuric acetate and sodium borohydride to yield the formula E-2 compound which is alkylated as described above to yield the formula E-3 compound. In Chart F, the formula F-1 compound, which is also a well known and readily available compound, is similarly converted to the formula F-3 compound as described above.

Compounds of the formulas II, III, or IV wherein V is $=CH_2$ and n is 0 are prepared as described, for example, in Thummel et al., J. Org. Chem. 42:2742 (1977) and Boger, et al., J. Org. Chem. 47:895 (1982).

Chart G depicts a method to prepare certain annelated pyridine intermediates to be used in Charts B and A. A phenethylamine of the formula G-1 is reacted with acetic anhydride to yield the formula G-2 compound. This compound is treated with polyphosphoric acid to yield the formula G-3 compound. This compound is treated with xylene in the presence of a palladium-on-carbon catalyst to yield the formula G-4 compound which is hydrogenated (e.g., by treatment under acidic conditions with hydrogen in a Parr apparatus in the presence of 85% platinum oxide catalyst) to yield the formula G-5 compound.

Chart H depicts a method of preparing the 2-mercaptobenzimidazoles used in Chart A. A substituted phenylenediamine compound of the formula H-1 (such compounds are well known and readily available or can be prepared by known means) is treated with potassium hydroxide and carbon disulfide to yield the formula H-2 compound. This is also described in Preparation 21.

Chart I depicts a method for preparing compounds of the formula I wherein V is S, n is 0 or 1, and the bicyclic substituent is of the formula B-1(a) and B-1(c). A pyridinyl ethanol or propanol of the formula I-1 (well known, readily available compounds) is treated with tert-butyldimethylsilyl chloride in an inert solvent to yield the formula I-2 product. This product is treated with methyl lithium to yield a mixture of 2- and 6-substituted products of the formula I-3. The silyl group is removed by treatment with acid, e.g., hydrochloric acid, to yield the formula I-4 product. Treatment of this product with thionyl chloride yields the formula I-5 chloride, which is then treated with meta-chloroperbenzoic acid to yield the formula I-6 N-oxide. The 2- and 6- isomers are conveniently separated by chromatography at this stage. Treatment of the I-6 N-oxide with sulfuric acid followed by fuming nitric acid yields the formula I-7 nitrate. Adding this product to a solution of ethanol in which hydrogen chloride gas has been bubbled yields the formula I-8 chloride. Reaction of this product with 2-mercaptobenzoxazole in acetonitrile yields the formula I-9 product, which is treated with sodium hydroxide in ethanol to yield the formula I-10 product. This product is then reacted as described in Chart B to yield the corresponding chloride, which is then converted to the final product as described in Chart A.

Chart J depicts a method for preparing compounds of the formula B-1(b) wherein V is S and n is 0 or 1. A compound of the Formula J-1, which can be prepared by known means, is oxidized with metachloroperbenzoic acid to afford N-oxide J-2. This N-oxide is reacted with 2-mercapto-1,3-benzoxazole in base to give J-3, and treated with sodium hydroxide in ethanol solvent to yield the cyclic thioether of the Formula J-4. The remaining steps starting with J-4 to the final compounds follow the same reaction procedures described in Chart I, i.e., I-10 to I-15.

All of the compounds of this invention are prepared by the procedures described above.

DESCRIPTION OF THE PREFERRED EMBODIMENTS

The present invention is seen more fully by the examples given below.

Preparation 1

5,6,7,8-Tetrahydro-2-methylquinoline

Refer to Chart C (conversion of C-1 to C-2).

7.8 g (54.55 mmol) of 2-methylquinoline, 40 ml 12N hydrochloric acid, and 1.00 g of platinumoxide are placed in a Parr apparatus and treated with hydrogen at a pressure of 50 psi. After approximately 20 hours, the mixture is diluted with 150 ml of water, filtered through Celite, neutralized to a pH of approximately 8 using potassium hydroxide, and extracted with chloroform to yield 6.30 g of titled product. The picrate has a mp of 158°–159° C. (See, Braun, et al. Ber, 56:1338 (1923) mp 154° C.).

Preparation 2

5,6,7,8-Tetrahydro-2-methylquinoline N-oxide

Refer to Chart B (conversion of formula B-1(c) to B-2).

1.303 g (8.86 mmol) of 5,6,7,8-tetrahydro-2-methylquinoline is dissolved in 50 ml of chloroform. To this is added dropwise over a period of 5 minutes 1.800 g (8.86 mmol) of 85% of m-chloroperbenzoic acid. The reaction is allowed to proceed for 2 hours. Afterwards the mixture is poured into 300 ml of chloroform, washed twice with sodium carbonate, once with saturated brine and worked up to yield 1.254 g of product exhibiting an NMR peaks ($CDCl_3$, $\delta$) at 7.00, 2.90, 2.50, and 1.85.

Preparation 3

5,6,7,8-Tetrahydro-2-acetoxymethylquinoline

Refer to Chart 8 (conversion of B-2 to B-3).

1.600 g (9.82 mmol) of the N-oxide of Preparation 2 is added to 10 ml of acetic anhydride and the solution heated in a 100° C. oil bath. After 30 minutes, 200 ml of crushed ice are added, the mixture is stirred for approximately 10–15 minutes and the pH is adjusted to approximately 8 with solid sodium bicarbonate. The mixture is extracted twice with chloroform, washed with brine, and worked up to yield 1.816 g of crude product. This mixture is separated using low pressure liquid chromatography (LPLC) using ethyl acetate-Skellysolve B (SSB—a commercial mixture of essentially N-hexane) to yield 0.628 g of titled product exhibiting an NMR peaks ($CDCl_3$, $\delta$) at 7.20, 5.20, 2.80, 2.17, and 1.80.

Preparation 4

5,6,7,8-Tetrahydro-2-hydroxymethylquinoline

Refer to Chart B (conversion of B-3 to B-4).

0.616 g (3.00 mmol) of the acetate prepared in Preparation 3, 10 ml of methanol, and 0.75 ml (3.27 mmol) of a 25% solution of sodium methoxide in methanol (4.37 mol) are stirred for one hour at 25° C. after which it is poured into 300 ml of chloroform, washed with water, saturated brine, and concentrated in vacuo to yield 0.559 g of a brownish crystalline product. This product is used without purification in the next step.

Preparation 5

5,6,7,8-Tetrahydro-2-chloromethylquinoline

Refer to Chart B (conversion of B-4 to B-5).

Approximately 3.00 mmol of the alcohol prepared in Preparation 4, 239 microliters (3.10 mmol) of methanesulfinylchloride, 460 microliters (3.30 mmol) of triethylamine, and 15 ml of methylene chloride are allowed to react for 26 hours. The mixture is diluted with 250 ml of chloroform, washed with water, brine, and concentrated in vacuo to yield 0.508 g of an orange, viscous oil. This product is used without purification in Example 1.

EXAMPLE 1

2-[(5,6,7,8-Tetrahydroquinolin-2-yl)methyl]thio-5-methoxybenzimidazole (Formula I: A is methoxy, B is hydrogen, X is =S, D is the formula IV substituent, n is one, V is $=CH_2$)

Refer to Chart A (conversion of A-1 and A-2 to A-3).

0.508 g (2.80 mmol) of the chloride of Preparation 5, 0.540 g (3.00 mmol) of 5-methoxy-2-mercaptobenzimidazole are dissolved in 18 ml of 95% ethanol to which is added 0.60 ml of 10 N sodium hydroxide. After warming approximately one hour in a 70° C oil bath, the product is worked up and separated using LPLC chromatography, using ethyl acetate SSB mixture (2:1) as eluant and collecting 20 ml fractions. Fractions 16–22 contained 0.862 g of the titled product as an oil. This oil exhibits NMR peaks ($CDCl_3$, δ) at 7.30, 4.30, 3.85, 3.05, 2.70, and 1.85.

EXAMPLE 2

2-[(5,6,7,8-Tetrahydroquinolin-2-yl)methyl]sulfinyl-5-methoxybenzimidazole (Formula 1: A is methoxy, B is hydrogen, X is =SO, D is the Formula IV substituent, V is $=CH_2$, and n is one)

Refer to Chart A (conversion of A-3 to A-4).

0.862 g (2.65 mmol) of the sulfide of Example 1, 30 ml of chloroform, 0.229 g (2.73 mmol) of sodium bicarbonate, and 0.554 g (2.73 mmol) of 85% m-chloroperbenzoic acid are reacted at a temperature of from 0° to 5° C. The product is worked up as in Example 1 and separated by LPLC using ethyl acetate-methanol (1800:40v/v) collecting 20 ml fractions. Fractions 16–28 yields 0.571 g of the titled product as an off-white or grayish solid having a melting point of approximately 72° C. and exhibiting an NMR peaks ($CDCl_3$, δ) at 7.10, 4.80, 3.80, 2.75 and 1.75.

Preparation 6

N-Acetyl-phenethylamine

Refer to Chart G (conversion of G-1 to G-2).

121.18 g of phenethylamine is dissolved in 450 ml of toluene in a 2 l three-necked flask. 102.09 g (95 ml) of acetic anhydride is added dropwise over a half hour period the temperature rises to 110° . After the addition is completed, the reaction solution temperature is maintained at approximately 95° C. The solvent is removed in vacuo and the residual oil was distilled under high vacuum (bp 160°–165° C./1mm) to afford 156.6 g of a white crystalline solid. The product exhibited NMR peaks ($CDCl_3$, δ) at 7.35, 3.45, 2.80, and 1.90.

Preparation 7

3,4-Dihydro-1-methylisoquinoline

Refer to Chart G (conversion of G-2 to G-3).

550–555 g of polyphosphoric acid was placed in a one liter three-necked flask fitted with a thermometer, mechanical stirrer, and nitrogen inlet. 65 g (0.40 mol) of the amide prepared in Preparation 6 are added in several portions. The temperature rises to approximately 225°–230° C. during this addition. After the addition is complete, the reaction temperature is maintained at 180°–185° C. for 2 hours. The reaction mixture is allowed to cool overnight. The mixture is then warmed and poured into 1.5 l of ice water, extracted with ether, neutralized with potassium hydroxide. The mixture is extracted with diethylether and dried over sodium sulfate, filtered, and concentrated in vacuo to yield 33.35 g of crude product, which was distilled (bp 65°–68°/1 atm) to give 24.02 g of the titled product. The product exhibits NMR peaks ($CDCl_3$, δ) at 7.35, 3.75, 2.80 and 2.35.

Preparation 8

1-Methylisoquinoline

Refer to Chart G (conversion of G-3 to G-4).

20.00 g (0.138 mol) of the 3,4-dihydro-2-methylisoquinoline of Preparation 7, 190 ml of o-xylene, and 2.4 g of 10% palladium-on-carbon catalyst are heated to 150° C in a round bottomed flask fitted with a condensor and magnetic stirring bar. The mixture is allowed to stir for 2 hours, cooled to room temperature, filtered, and the solid cake washed with 30–50 ml of benzene. The xylene is removed at 60° C. under vacuum and the resulting yellow liquid is distilled (bp 75°–77° C., 1 atm) to yield 10.086 g of a colorless liquid exhibiting characteristic NMR peaks ($CDCl_3$, δ) at 2.90 and 2.40. NMR analysis of this product indicates that it is a 2:1 mixture of 1-methylisoquinoline and 5,6,7,8-tetrahydro-1-methylisoquinoline.

Preparation 9

5,6,7,8-Tetrahydro-1-methylisoquinoline

Refer to Chart G (conversion of G-4 to G-5).

6.60 g of the mixture of Preparation 8, 30 ml of 12 N hydrochloric acid, and 0.800 g of platinum oxide catalyst are placed in a Parr apparatus at 50 psi of hydrogen gas. After approximately 4 hours, the hydrogenation is stopped, and the product is worked up as described above, yielding the titled product in quantitative yield which exhibits NMR peaks ($CDCl_3$, δ) at 8.25, 6.85, 2.60, 2.40, and 1.80.

Preparation 10

5,6,7,8-Tetrahydroisoquinoline

Refer to Chart C (conversion of C-1 to C-2).

4.335 g of isoquinoline, 30 ml of 12 N hydrochloric acid, and 0.800 g of platinum oxide catalyst are placed in a Parr apparatus at 50 psi of hydrogen gas. The reaction is allowed to proceed for approximately 17 hours after which it is worked up as described above yielding 3.916 g of a yellow liquid exhibiting NMR peaks ($CDCl_3$, δ) at 8.40, 8.35, 7.00, 2.70, and 1.80.

Preparation 11

5,6,7,8-Tetrahydro-1-methylisoquinoline (methylation of C-2 product)

2.155 g (16.20 mmol) of 5,6,7,8-tetrahydroisoquinoline, 20 ml of diethylether, and 13 ml (19.50 mmol) of a 1.5 molar solution of methyllithium-lithium bromide complex in diethylether are reacted for approximately 16 hours at 45° C. The excess methyllithium is destroyed by cautious addition of water, and the crude product is obtained by chloroform extraction. Removal of the chloroform in vacuo gives the crude product which is purified by LPLC (methylene chloride-acetone, 4:1) to give 1.00 g of product. The product exhibits NMR peaks ($CDCl_3$, δ) at 8.25, 6.85, 2.65, 2.5, and 1.80.

Preparation 12

5,6,7,8-Tetrahydro-1-methylisoquinoline, N-oxide

Refer to Chart B (conversion of B-1(a) to B-2).

2.381 g of 1-methyl-tetrahydroisoquinoline, prepared as described in Preparation 11, 12 ml of acetic acid, and 3 ml of a 30% solution hydrogen peroxide are reacted for approximately 6 hours after which one additional ml of 30% hydrogen peroxide is added. An additional ml of 30% hydrogen peroxide is added 14 hours later, and the reaction is stopped 2 hours after that. The mixture is diluted with crushed ice, water, the pH is adjusted to approximately 9–10 with potassium hydroxide, and the solution is extracted with chloroform, washed with brine, and worked up to yield 2.374 g of crude product. The final product (1.00 g; mp 80°–83° C.) is obtained by trituration with hexane and removed by filtration of the insoluble N-oxide product from unreacted starting material.

Preparation 13

5,6,7,8-Tetrahydro-1-acetoxymethylisoquinoline

Refer to Chart B (conversion of B-2 to B-3).

0.499 g of the N-oxide prepared in Preparation 12, and 4.0 ml of acetic anhydride are heated at 100° C. for 30 minutes and 140° C. for 10 minutes. The mixture is cooled, crushed ice water is added, and the mixture is neutralized with saturated sodium bicarbonate to a pH of approximately 8. The solution is extracted twice with chloroform, washed with brine, and worked up to yield a dark brown viscous oil. This crude product is chromatographed using LPLC with a 7:1 mixture of methylene chloride-acetone to yield 0.3000 g of the title compound which exhibits NMR peaks ($CDCl_3$, δ) at 5.30 and 2.20.

Preparation 14

5,6,7,8-Tetrahydro-1-hydroxymethylisoquinoline

Refer to Chart B (conversion B-3 to B-4).

0.419 g (2.04 mmol) of the acetate of Preparation 13 dissolved in 8 ml of methanol are treated with 0.48 ml of a 25% sodium methoxide in methanol. The mixture is stirred at 25° C. for 30 minutes and then diluted with 250 ml of chloroform, washed with 75 ml of water, dried, and concentrated in vacuo to yield 0.286 g of a solid. This product is chromatographed using LPLC using 100% ethyl acetate as eluant, and collecting 15 ml fractions. Fractions 8–15 yielded 0.16 g of the titled white crystalline solid. This solid exhibited NMR peaks ($CDCl_3$, δ) at 8.30, 7.00, 4.60, 2.80, 2.50, and 1.80.

Preparation 15

5,6,7,8-Tetrahydro-1-chloromethylisoquinoline

Refer to Chart B (conversion of B-4 to B-5).

0.106 g (0.65 mmol) of the alcohol of Preparation 14, 58 μl (0.75 mmol) of methanesulfonyl chloride, 111 μl (0.80 mmol) of triethylamine and 4 ml of methylene chloride are allowed to react for approximately 41 hours at 25° C. after which time the mixture is diluted with 250 ml of chloroform, and extracted with water, chloroform, and brine, dried, and concentrated in vacuo to yield 0.106 g of product which is used in Example 3 without further purification.

EXAMPLE 3

2-[(5,6,7,8-Tetrahydroisoquinolin-1-yl)methyl]thio-5-methoxybenzimidazole (Formula I: A is methoxy., B is hydrogen, X is =S, D is the Formula II substituent, V is $=CH_2$, and n is one)

Refer to Chart A (conversion of A-1 and A-2 to A-3).

0.135 g (0.75 mmol) of 5-methoxy-2-mercaptobenzimidazole (Preparation 21), 0.65 mmol of the chloride of Preparation 15, 5 ml of 95% ethanol, 150 μl (1.50 mmol) of 10 N sodium hydroxide are allowed to react at 70° C. for approximately 1 hour. The mixture is then diluted with 200 ml of chloroform, washed with 0.5 N sodium hydroxide, extracted with chloroform, washed with 1 N sodium hydroxide, saturated brine, the chloroform extract is dried over sodium sulfate, concentrated in vacuo to yield 0.228 g of the title product, an oil, which solidifies at 0–5° C. and exhibits NMR peaks ($CDCl_3$, δ) at 4.40, 3.80, 2.70 and 1.75.

EXAMPLE 4

2-[(5,6,7,8-Tetrahydroisoquinolin-1-yl)methyl]sulfinyl-5-methoxybenzimidazole (Formula I: A is methoxy, B is hydrogen, X is =SO, D is the Formula II substituent, V is $=CH_2$, and n is one)

Refer to Chart A (conversion of A-3 to A-4).

Approximately 0.228 g (0.65 mmol) of the sulfide of Example 3, 7 ml of chloroform, 55 mg (0.65 mmol) of sodium bicarbonate, and 0.122 g (0.60 mmol) of an 85% m-chloroperbenzoic acid are reacted as described in Example 2 to yield 0.312 g of an oil. This product is chromatographed on LPLC using ethyl acetate-methanol (1800:60 v/v) collecting 25 ml fractions. Fractions 16–27 yield 0.155 g of the titled product as a gray off-white solid, melting point 134-135° C. High resolution mass spectrum: Calcd. for $C_{18}H_{19}N_3O_2S$: 341.1198; Found: 341.1188.

Preparation 16

5-Methyl-6-azachroman

Refer to Chart D (conversion of D-5 to D-6).

To 2.45 g (18.15 mmol) of 6-azachroman (prepared as described in Sliwa, et al., J. Het. Chem. 12:809 (1975)) in 25 ml of ethyl ether is added 61 ml of 1.5 M methyllithium-lithium bromide complex. The mixture is heated at reflux for 17 hours and worked up as described above to yield 0.800 g of the titled compound. High resolution mass spectrum: Calcd. for $C_9H_{11}NO$: 149.0841; Found: 149.0834.

Preparation 17

5-Methyl-6-azachroman, N-oxide

Refer to Chart B (conversion of B-1(a) to B-2).

Following the m-chloroperbenzoic acid oxidation procedure of the preceding examples, and employing 0.628 g (2.44 mmol) of the product of Preparation 16, the corresponding N-oxide is prepared using the method of Chart B. The yield is 0.470 g. High resolution mass spectrum: Calcd. for $C_9H_{11}NO_2$: 165.0790; Found: 165.0784.

Preparation 18

5-Acetoxymethyl-6-azachroman

Refer to Chart B (conversion of B-2 to B-3).

Following the procedures of the preceding examples, and those depicted in Chart B, the titled compound is prepared from 0.440 g (2.67 mmol) of the product of Preparation 17. The yield is 316 mg of a colorless oil. High resolution mass spectrum: Calcd. for $C_{11}H_{13}NO_3$: 207.0845; Found: 207.0891.

Preparation 19

5-Hydroxymethyl-6-azachroman

Refer to Chart B (conversion of B-3 to B-4).

Following the procedure of the preceding examples, and employing the process depicted in Chart B, the titled alcohol is prepared from 0.315 g (1.52 mmol) of the product of Preparation 18. The yield is 201 mg of a crystalline solid. High resolution mass spectrum: Calcd. for $C_9H_{11}NO_2$: 165.0790; Found: 165.0784.

Preparation 20

5-Chloromethyl-6-azachroman

Refer to Chart B (conversion of B-4 to B-5).

Following the procedure of the preceding examples, and employing 0.201 g (1.22 mmol) of the alcohol of Preparation 19. The crude yield is 248 mg of an orange oil, which was used directly in the next reaction.

EXAMPLE 5

2-[(6-Azachroman-5-yl)methyl]thio-5-methoxybenzimidazole (Formula 1: A is methoxy, B is hydrogen, X is =S, D is the Formula II substituent, V is =0, and n is one)

Refer to Chart A (conversion of A-1 and A-2 to A-3).

Following the procedures of Examples 1 and 3, and the method depicted in Chart A, the titled compound is prepared from 0.219 g (1.29 mmol) of the compound of Preparation 21 and 0.223 g (1.22 mmol) of the compound of Preparation 20. The yield is 0.340 g. High resolution mass spectrum: Calcd. for $C_{17}H_{17}N_3O_2SK$: 366.0679; Found: 366.0675.

EXAMPLE 6

2-[(6-Azachroman-5-yl)methyl]sulfinyl-5-methoxybenzimidazole (Formula 1: A is methoxy, B is hydrogen, X is =SO, D is the formula II substituent, V is =0, and n is one)

Refer to Chart A (conversion of A-3 to A-4).

Following the procedures of Examples 2 and 4, and the procedure depicted in Chart A, the titled crystals are prepared from 0.284 g (0.868 mmol) of the compound of Example 5. The yield is 195 mg. High resolution mass spectrum: Calcd. for $C_{17}H_{17}N_3O_3SK$: 382.0628; Found: 382.0636.

EXAMPLE 7

2-[(6-Azachroman-5-yl)methyl]thiobenzimidazole (Formula I: A and B are hydrogen, X is =S, D is the formula II substituent, V is =0, and n is one)

Refer to Chart A (conversion of A-1 and A-2 to A-3).

Following the procedures of Examples 1, 3, and 5, and using 0.065 g (0.432 mmol) of 2-mercaptobenzimidazole and 0.079 g (0.432 mmol) of the product of Preparation 25, the titled compound is prepared. The yield is 72 mg of a white solid. High resolution mass spectum: Calcd. for $C_{16}H_{16}N_3OS$: 298.1014; Found: 298.0996.

EXAMPLE 8

2-[(6-Azachroman-5-yl)methyl]sulfinylbenzimidazole (Formula I: A and B are hydrogen, X is =SO, D is the Formula II substituent, V is =0, and n is one)

Refer to Chart A (conversion of A-3 to A-4).

Following the procedures of Examples 2, 4and 6, and employing 0.072 g (0.242 mmol) of the product of Example 7, the titled crystals are prepared. The yield is 40 mg. High resolution mass spectum: Calcd. for $C_{16}H_{15}N_3O_2SK$: 352.0522; Found: 352.0532.

Preparation 21

5-Methoxy-2-mercaptobenzimidazole

Refer to Chart H (conversion of H-1 to H-2).

To a magnetically stirred solution of 4-methoxy-o-phenylenediamine hydrochloride (20.0 g, 0.115 mol) in 400 ml of ethanol-water (4:1) is added 2 molar equivalent of 85% potassium hydroxide solution and 20 ml of carbon disulfide. The contents are warmed in a 75°-80° C. oil bath for 2.5 hours and the solvent is removed in vacuo. To the residual thick slurry is added 200 ml of water, the contents heated to boiling, and 95% ethanol is added until a transparent solution is obtained. The solution is filtered, the filtrate is allowed to stand at 25° C. and the resulting cyrstalline solid is collected, and washed with water-ethanol. Drying in vacuo affords 11.0 g of the titled crystals mp 253°-254.2° C. Concentration of the mother liquor and silica chromatography (280 g, acetone-methylene chloride, 1:6) gives an additional 3.9 g of product (total 14.9 g, 72% yield).

Preparation 22

Refer to Chart I (conversion of I-1 to I-2)

47.85 ml (0.365 mol) of 3-(3-pyridyl)-1-propanol is dissolved in 200 ml of dimethylformamide and is then added to 31.02 g (0.456 mol) of imidazole and 58.10 g (0.383 mol) of tert-butyldimethylsilyl chloride. Stirring is continued at room temperature for 2 hours. At the end of this period, the reaction is diluted with 500 ml of water and extracted with ether. The extracts are dried over anhydrous sodium sulfate and the solvent removed in vacuo to give 103 g. of an oil which is chromatographed on 600 g of silica gel. Elution with Skellysolve B-ethyl acetate (3:1) affords 90.87 g of the titled product. The product exhibits NMR peaks ($CDCl_3$, δ) at 8.50, 3.60, 0.85 and by TLC shows Rf at 0.35 in Skellysolve B-ethyl acetate (2:1).

Preparation 23

Refer to Chart I (conversion of I-2 to I-3)

To 480 ml of 1.5M methyl lithium (0.720 mol) in ether is added 90.8 g (0.360 mol) of the compound of Preparation 22. The reaction is then heated at reflux for 24 hours. At the end of this period, the reaction mixture is diluted with 1500 ml of ether, and carefully treated with 125 ml of saturated sodium sulfate solution. The ether solution is decanted from the resulting solid residue and the ether is dried over anhydrous sodium sulfate. Concentration of the solvent in vacuo gives 50.14 g of a yellow oil. The crude product is chromatographed on 500 g of silica gel. Elution with Skellysolve B-acetone (4:1) affords 28.4 g of I-3 as a mixture of 2-methyl and 6-methyl isomers. The mixture exhibits NMR peaks ($CDCl_3$, δ) at 2.46 and 2.50 and by TLC shows Rf at 0.50 and 0.42 in Skellysolve B-acetone (4:1).

Preparation 24

Refer to Chart I (conversion of I-3 to I-4)

The product (28.4 g, 0.107 mol) obtained in Preparation 23 is dissolved in 60 ml of methanol and 107 ml of 2N hydrochloric acid is added. The mixture is stirred at 25° for 30 minutes. The mixture is then diluted with chloroform and neutralized with saturated sodium bicarbonate solution and solid potassium carbonate. The chloroform solution is separated and dried over anhydrous sodium sulfate. Concentration of the solvent in vacuo gives 31.07 g of a yellow oil. The crude product is chromatographed on 300 g of silica gel. Elution with acetone-methylene chloride (1:1) yields 14.25 g of I-4, an oil, as a mixture of 2-methyl and 6-methyl isomers. The mixture exhibits NMR peaks ($CDCl_3$, δ) at 3.75, 2.49 and 2.57 and by TLC shows Rf at 0.26 in acetone-methylene chloride (1:1).

Preparation 25

Refer to Chart I (conversion of I-4 to I-5)

14.25 g (94.37 mmol) of the product obtained in Preparation 24 is dissolved in 100 ml of chloroform. To this solution is added over a period of 17 minutes 10.33 ml (141.6 mmol) of thionyl chloride dissolved in 15 ml of chloroform. The reaction is then heated at reflux for 30 minutes. At the end of this time, the reaction mixture is poured into 150 ml of crushed ice, made basic to pH=8 with 45% potassium hydroxide solution, extracted with chloroform, and the chloroform solution dried over anhydrous sodium sulfate. Concentration in vacuo gives an oil which is chromatographed on 160 g of silica gel. Elution with Skellysolve B-acetone (2:1) affords 15.41 g of I-5, a tan oil, as a mixture of 2-methyl and 6-methyl isomers. The mixture exhibits NMR peaks ($CDCl_3$, δ) at 3.55, 2.53 and 2.60 and by TLC shows Rf at 0.29 and 0.25 in Skellysolve B-acetone (3:1).

Preparation 26

Refer to Chart I (conversion of I-5 to I-6)

The product (15.41 g, 91.18 mmol) obtained in Preparation 25 is dissolved in 160 ml of chloroform and 20.20 g (93.92 mmol) of 80% meta-chloroperbenzoic acid is added portionwise over a 5 minute period. Stirring at 25° C. continues for 30 minutes. The reaction is poured into 400 ml of chloroform and successively washed with 10% sodium sulfite, saturated sodium bicarbonate and brine and the chloroform solution is dried over anhydrous sodium sulfate. Concentration of the solvent in vacuo yields 16.50 g of an oil. The crude product is chromatographed on 1 kg of silica gel. Elution with acetone-chloroform (1:1) containing 1-10% methanol gives initially 5.11 g of the 6-methyl isomer and then 8.48 g of I-6, the 2-methyl isomer. The I-6 product exhibits NMR peaks ($CDCl_3$, δ) at 8.30, 3.60 and 2.57 and by TLC shows Rf at 0.30 in acetone-chloroform (1:1) containing 5% methanol.

The 6-methyl isomer exhibits NMR peaks ($CDCl_3$, δ) at 8.20, 3.50 and 2.53 and by TLC shows Rf at 0.40 in the same solvent as above.

Preparation 27

Refer to Chart I (conversion of 1-6 to I-7)

To a magnetically stirred solution of 20 ml of concentrated sulfuric acid is added portionwise 8.48 g (45.84 mmol) of the product obtained in Preparation 26. When the internal reaction temperature reaches 65° C., 10 ml of 90% fuming nitric acid is added over a 4 minute period. The reaction contents are then heated in an oil bath at 100° C. for 1.5 hours. At the end of this period, the reaction mixture is poured onto 200 ml of crushed ice, made basic to pH 8 with 72 ml of 45% potassium hydroxide. The aqueous solution is extracted with chloroform, the chloroform washed with brine and dried over anhydrous sodium sulfate. Concentration of the solvent in vacuo gives an oil which is chromatographed on 125 g of silica gel. Elution with methylene chloride-acetone (3:1) yields 6.06 g of I-7 as a yellow solid. The product exhibits NMR peaks ($CDCl_3$, δ) at 8.35, 7.85 and 2.60 and by TLC shows Rf at 0.60 in acetone-chloroform (1:1) containing 5% methanol.

Preparation 28

Refer to Chart I (conversion of I-7 to I-8)

Hydrogen chloride gas is bubbled into 150 ml of absolute ethanol for 15 minutes. The product (6.06 g, 26.35 mmol) obtained from Preparation 27 is dissolved in 25 ml of hot ethanol and added to the hydrogen-chloride-ethanol solution. The reaction mixture is then heated at reflux for 4 hours. The reaction is cooled to room temperature, treated with 20 ml of saturated sodium bicarbonate solution and solid potassium carbonate until the evolution of carbon dioxide gas stops. The mixture is extracted thoroughly with chloroform, and the chloroform extract dried over anhydrous sodium sulfate. Concentration of the solvent in vacuo affords an oil which is chromatographed on 200 g of silica gel. Elution with acetone-chloroform (1:1) containing 3% methanol yields 5.17 g of I-8 as a yellow solid. The product exhibits NMR peaks ($CDCl_3$, δ) at 8.20, 7.20, 2.60 and by TLC shows Rf at 0.34 in acetone-chloroform (1:1) containing 5% methanol.

Preparation 29

Refer to Chart I (conversion of I-8 to 1-9)

The product (5.17, 23.61 mmol) obtained from Preparation 28 is dissolved with stirring in 100 ml of acetonitrile. To this solution is added 7.13 g (47.21 mmol) of 2-mercaptobenzoxazole and 7.20 ml (51.94 mmol) of triethylamine. The contents are heated at reflux for 3 hours. At the end of this period, the reaction is allowed to cool to room temperature, diluted with 700 ml of chloroform, the chloroform is washed with 0.5 N sodium hydroxide solution and saturated brine and then dried over anhydrous sodium sulfate. Concentration of the solvent in vacuo gives 7.73 g of I-9 as a brown oil, which is used in Preparation 30 without further purification. The product exhibits NMR peaks ($CDCl_3$, δ) at 8.15, 3.40, 2.57 and by TLC shows Rf at 0.32 in acetone-chloroform (1:1) containing 5% methanol.

Preparation 30

Refer to Chart I (conversion of I-9 to I-10)

To a magnetically stirred solution of the product 8.05 g (24.10 mmol) in 150 ml of 95% ethanol obtained in Preparation 29 is added 4.82 ml of 1ON sodium hydroxide. The reaction is then heated at reflux for 2 hours. At the end of this time, the reaction is cooled to room temperature, diluted with chloroform, the chloroform solution is washed with water and brine and dried over anhydrous sodium sulfate. Concentration of the solvent in vacuo gives an oil which is chromatographed on 325 g of silica gel. Elution with 5% methanol in chloroform-actone (1:1) yields 2.92 g of I-10 as a crystalline white solid. The product exhibits NMR peaks ($CDCl_3$, δ) at 8.05, 6.90, 3.00, 2.53 and by TLC shows Rf at 0.26 with 10% methanol in chloroform-actone (1:1).

Preparation 31

Refer to Chart I (conversion of I-10 to I-11)

Following the same procedure as described for Preparation 13, 2.92 g (16.13 mmol) of I-10 gives 2.44 g of I-11 as a yellow oil. The product exhibits NMR peaks ($CDCl_3$, δ) at 8.20, 7.05, 5.20, 2.17 and by TLC shows Rf at 0.29 in Skellysolve B-actone (3:1).

Preparation 32

Refer to Chart I (conversion of I-11 to I-12)

Following the same procedure as described for Preparation 14, 2.44 g (10.94) of I-11 yields 1.96 g of I-12 as a white crystalline solid, mp 97°-99° C. The product exhibits NMR peaks ($CDCl_3$, δ) at 4.63, 3.00, 2.60, 2.15 and by TLC shows Rf at 0.21 in Skellysolve B-actone (3:1).

Preparation 33

Refer to Chart I (conversion of I-12 to I-13)

Following the same procedure as described for Preparation 15, 1.96 g (10.83 mmol) of 1-12 affords 2.11 g of 1-13 as a reddish oil. The product by TLC shows Rf at 0.60 in methylene chloride-actone (6:1) and is used directly in the next step without further purification.

EXAMPLE 9

2-[(5-Thia-5,6,7,8-tetrahydroisoquinolin-1-ylmethyl)thio]-benzimidazole (Formula I: A and B are hydrogen, X=S, D is the Formula II substituent, V is =S, n is 1)

1.59 g (10.60 mmol) of 2-mercaptobenzimidazole is placed in 35 ml of 95% ethanol and 2.11 g (10.60 mmol) of the product obtained in Preparation 33 dissolved in 20 ml of 95% ethanol and 2.12 ml of 10N sodium hydroxide solution are added. The reaction is heated at reflux for 0.5 hours. At the end of this time, the reaction mixture is allowed to cool to room temperature, diluted with chloroform, and the chloroform solution is washed with water, 0.5N sodium hydroxide solution and brine and dried over anhydrous sodium sulfate. Concentration of the solvent in vacuo gives a crystalline solid. Recrystallization from ethyl acetate-actone-methanol (1:1:0.1) solvent yields 3.20 g of product, mp 211°-212° C. High resolution mass spectrum: Calcd. for $C_{16}H_{15}N_3S_2K$: 352.0344; Found: 352.0346. C, H analysis: Calcd for C, 61.34; H, 4.79; N, 13.42; S, 20.45; Found: C, 60.78; H, 4.94; N, 12.99; S, 19,93. The product by TLC shows Rf at 0.43 in chloroform-actone (3:1).

EXAMPLE 10

2-[(5-Thia-5,6,7,8-tetrahydroisoquinolin-1-ylmethyl)sulfinyl]-benzimidazole (Formula I: A and B are hydrogen, X is =SO, D is the Formula II substituent, V is =S, n is 1)

Following the procedures of Examples 2, 4, 6 and 8 and employing 1.124 g (3.59 mmol) of the product of Example 9, the titled crystals are prepared. The yield is 0.644 g, mp 161°-162° C. (from ethyl acetate-acetone-methanol). High resolution mass spectrum: Calcd. for $C_{16}H_{16}N_3OS_2K$: 368.0294; Found: 368.0286. C,H analysis: Calcd. for $C_{16}H_{15}N_3OS_2$: C, 58.36; H, 4.56; N, 12.77; S, 19.45. The product exhibits NMR peaks ($CDCl_3$, δ) at 8.20, 4.80, 3.00-2.70, 2.10 and by TLC shows Rf at 0.42 with 2% methanol in acetone-chloroform (1:1).

EXAMPLE 11

2-[(5,6,7,8-Tetrahydroquinoline-2-yl)methyl]sulfinylbenzimidazole (Formula I: A and B are hydrogen, X is =SO, D is the formula IV substituent, V is —$CH_2$, and n is one)

Refer to Chart A, scheme 2.

2-[Lithium-methylsulfinyl]benzimidazole (0.1 mol) is dissolved in 150 ml of benzene and 0.1 mol of 1-chloro-5,6,7,8-tetrahydroisoquinoline are added and the mixture refluxed for 2 hr. The lithium chloride is filtered off, and the solution is concentrated in vacuo. The residue is crystallized from ether and recrystallized from ethyl acetate, acetone, or ethyl acetate-acetone solvent mixtures.

EXAMPLE 12

2-[(5-oxa-5,6,7,8-tetrahydroisoquinolin-1-ylmethyl)sulfinyl]-5-trifluoromethylbenzimidazole Refer to Chart A, scheme 3.

22.1 g (0.10 mol) of 5-trifluoromethyl-2-chlorobenzimidazole and 19.91 g (0.11 mol) of 3,4-dihydro-2H-pyrano[3,2-c]-2-thiomethylpyridine in 250 ml of isopropanol are heated under reflux for 10 hours. The solvent is removed in vacuo and ice water is added to the residue. The resulting solid is removed by filtration and then oxidized following the procedures of Examples 2, 4, 6, 8 and 10 to yield the title compound, mp 160° C. (dec.).

EXAMPLE 13

2-[(5-thia-5,6,7,8-tetrahydroisoquinolin-1-ylmethyl)sulfinyl]-5-trifluoromethylbenzimidazole Refer to Chart A, scheme 4.

1.76 g (8.0 mmol) of 5-trifluoromethyl-o-phenylenediamine and 2.17 g (9.0 mmol) of 3,4-dihydro-2H-thiopyrano[3,2-c]-2-carboxythiomethylpyridine are heated under reflux for 2 hours in 20 ml of 4N hydrochloric acid. The mixture is neutralized with ammonia. The solution is then extracted with chloroform, the chloroform removed in vacuo and the resulting product oxidized following the procedures in Examples 2, 4, 6, 8, 10, and 12 to give the title compound.

EXAMPLE 14

Following the procedures of Charts A-J, as depicted in the preceeding Examples, the following compounds are prepared:

2-[(5-thia-5,6,7,8-tetrahydroisoquinolin-3-ylmethyl)-sulfinyl]benzimidazole;
2-[(5-oxa-5,6,7,8-tetrahydroisoquinolin-3-ylmethyl)-sulfinyl]benzimidazole;
2-[5,6,7,8-tetrahydroisoquinolin-3-ylmethyl)-sulfinyl]-benzimidazole;
2-[(8-thia-5,6,7,8-tetrahydroisoquinolin-3-ylmethyl)-sulfinyl]benzimidazole;
2-[(8-oxa-5,6,7,8-tetrahydroisoquinolin-3-ylmethyl)-sulfinyl]benzimidazole;
2-[(3,4-dihydrothieno[3,2-c]-pyridin-2-ylmethyl)-sulfinyl]benzimidazole;
2-[(3,4-dihydrofuro[3,2-c]-pyridin-2-ylmethyl)-sulfinyl]benzimidazole;
2-[(5,6-dihydrothieno[3,2-d]-pyridin-2-ylmethyl)-sulfinyl]benzimidazole; and
2-[(5,6-dihydrofuro[3,2-d]-pyridin-2-ylmethyl)-sulfinyl]benzimidazole.

FORMULAS

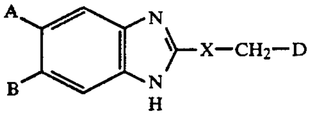
I

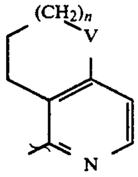
II

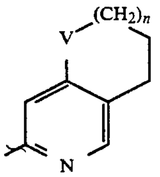
III

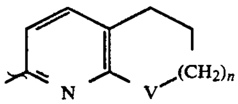
IV

CHART A

Scheme 1

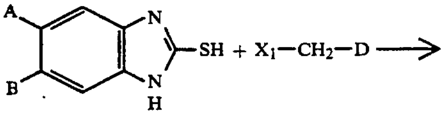
A-1 A-2

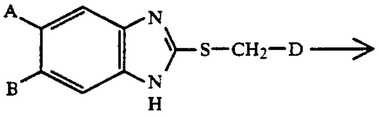
A-3

-continued

CHART A

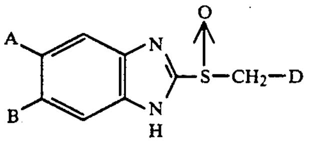
A-4

Scheme 2

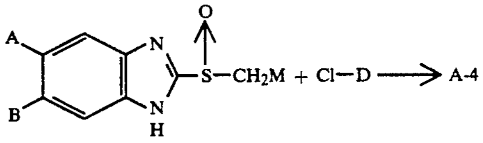
A-5 A-6

Scheme 3

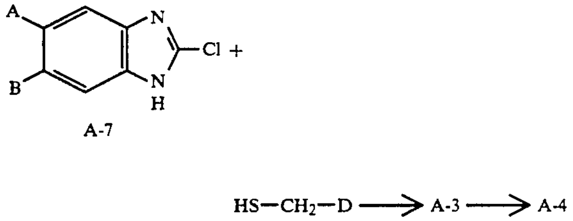
A-7

A-8

Scheme 4

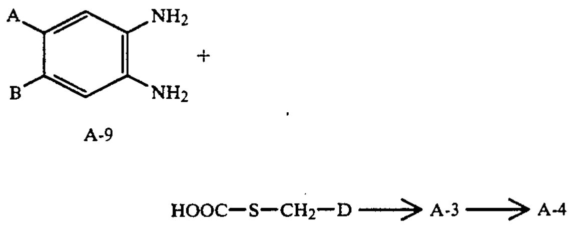
A-9

A-10

CHART B

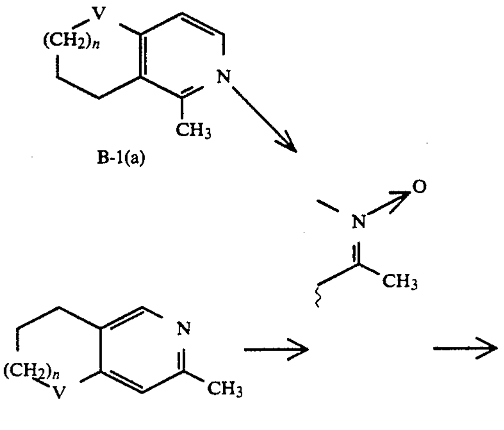
B-1(a)

B-1(b) B-2

-continued
CHART B
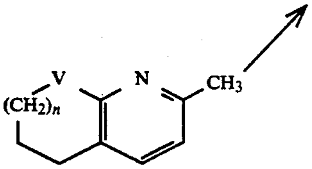
B-1(c)
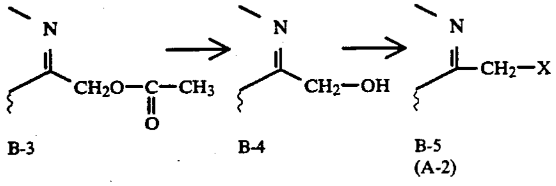
B-3 B-4 B-5 (A-2)
CHART C
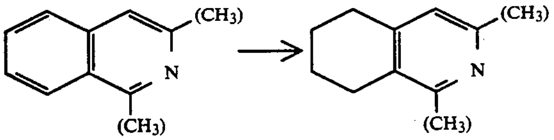
C-1 C-2
CHART D
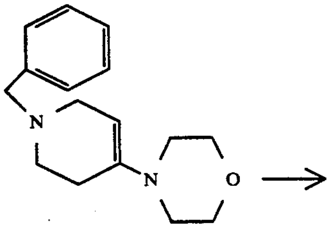
D-1
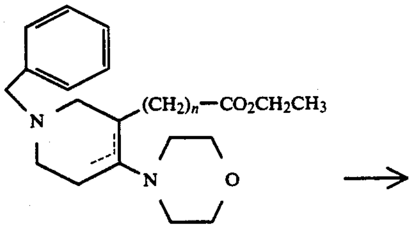
D-2
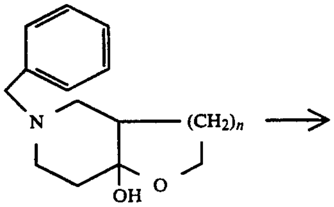
D-3
-continued
CHART D
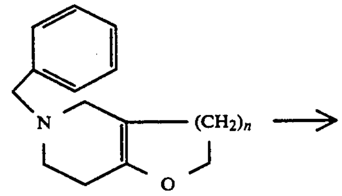
D-4
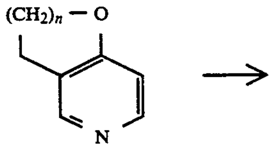
D-5
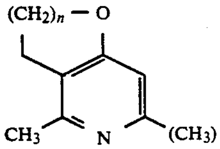
D-6
CHART E
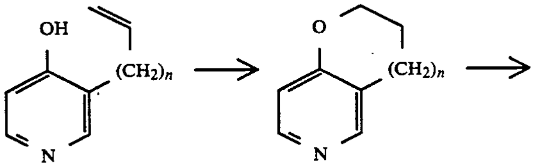
E-1 E-2
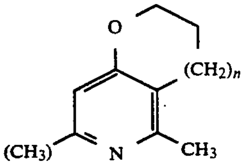
E-3
CHART F
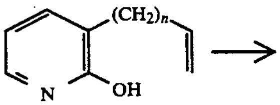
F-1
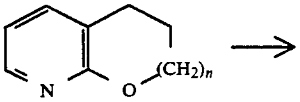
F-2

-continued
CHART F
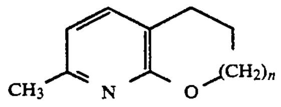
CHART G
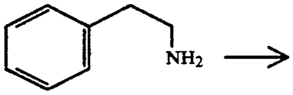
G-1
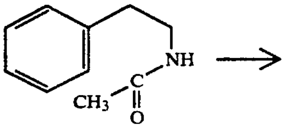
G-2
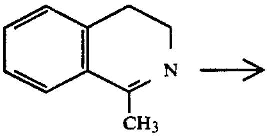
G-3
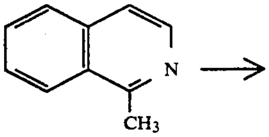
G-4
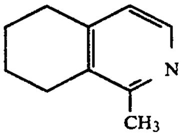
G-5
CHART H
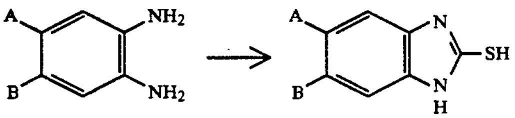
H-1 H-2
CHART I
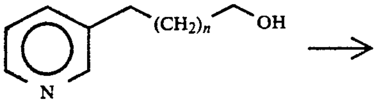
I-1
-continued
CHART I
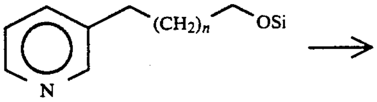
I-2
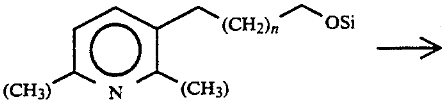
I-3
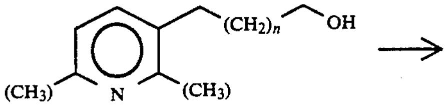
I-4
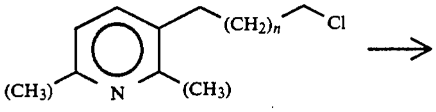
I-5
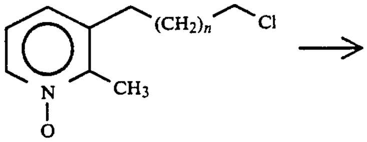
I-6
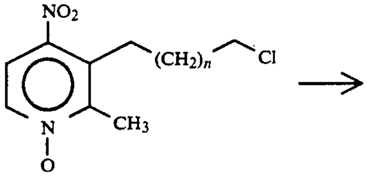
I-7
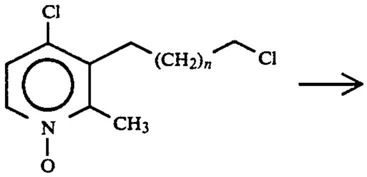
I-8
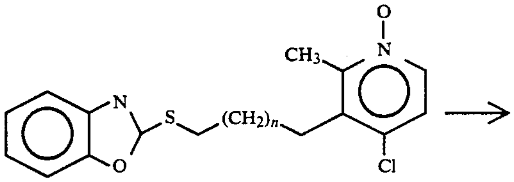
I-9

-continued
CHART I
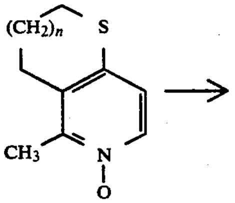
I-10
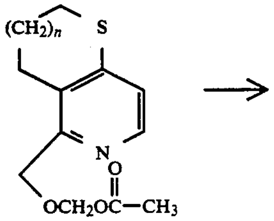
I-11
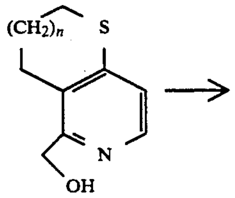
I-12
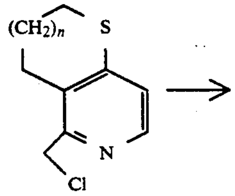
I-13
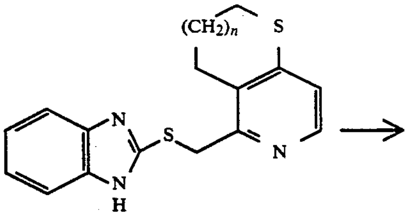
I-14
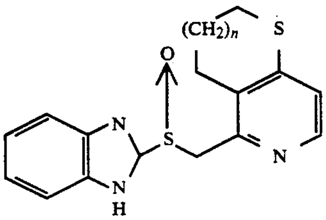
I-15
CHART J
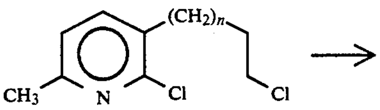
J-1
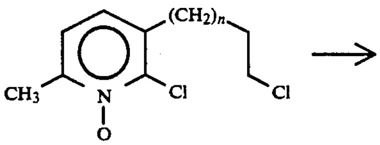
J-2
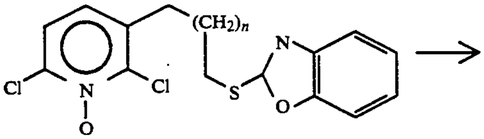
J-3
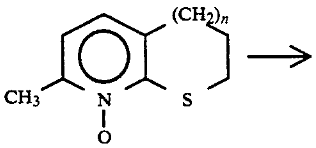
J-4
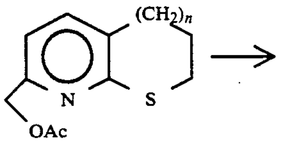
J-5
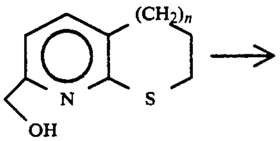
J-6
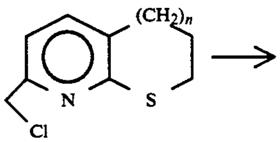
J-7
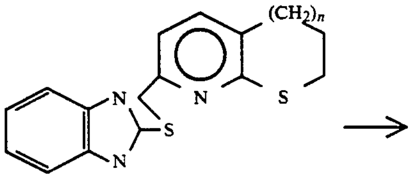
J-8

-continued

CHART J

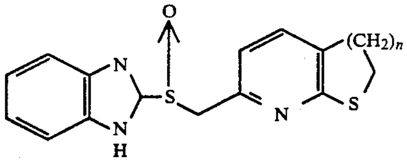

I claim:

1. A compound of the formula I:

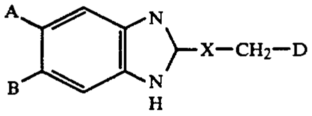

wherein X is (a) =S, or (b) =SO;

wherein A and B are the same or different and are (a) hydrogen, (b) $-OR_1$, (c) $-COR_1$, (d) $-CO_2R_1$, or (e) $-CO_2M$;

wherein $R_1$ is $C_1$-$C_4$ alkyl;

wherein M is a pharmacologically acceptable cation;

wherein D is a bicyclic substituent of the formula II, III, or IV

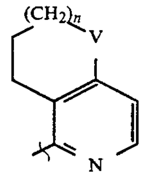

II

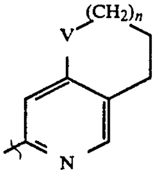

III

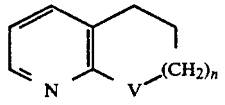

IV wherein V is (a) =O, or (b) =S, and wherein n is zero or one.

2. A compound of claim 1, wherein A and B are hydrogen, X is =SO, and D is a bicyclic substituent of the Formula II.

3. 2-[(6-Azachroman-5-yl)methyl]sulfinylbenzimidazole, a compound of claim 2.

4. 2-[(6-Azachroman-5-yl)methyl]thio-5-methoxybenzimidazole, a compound of claim 1.

5. 2-[(6-Azachroman-5-yl)methyl]sulfinyl-5-methoxybenzimidazole, a compound of claim 1.

6. 2-[(6-Azachroman-5-yl)methyl]thiobenzimidazole, a compound of claim 1.

7. 2-[(5-Thia-5,6,7,8-tetrahydroisoquinolin-1-ylmethyl)-thio]-benzimidazole, a compound of claim 1.

8. 2-[(5-Thia-5,6,7,8-tetrahydroisoquinolin-1-ylmethyl)-sulfinyl]-benzimidazole, a compound of claim 1.

* * * * *